United States Patent [19]

Houbiers et al.

[11] 4,262,129

[45] Apr. 14, 1981

[54] PREPARATION OF A 3-THIENYLMALONIC ACID AND THE CORRESPONDING DIESTERS

[75] Inventors: Joannes P. M. Houbiers, Tegelen; Petrus G. Müris, Venlo, both of Netherlands

[73] Assignee: Océ-Andeno B.V., Venlo, Netherlands

[21] Appl. No.: 75,267

[22] Filed: Sep. 13, 1979

Related U.S. Application Data

[63] Continuation-in-part of Ser. No. 963,980, Nov. 24, 1978, abandoned.

[30] Foreign Application Priority Data

Dec. 6, 1977 [GB] United Kingdom ............... 50750/77

[51] Int. Cl.$^3$ .......................................... C07D 333/24
[52] U.S. Cl. .................................................. 549/79
[58] Field of Search ........................................ 549/79

[56] References Cited

PUBLICATIONS

Wagner & Zook, Synthetic Organic Chemistry, (1965), pp. 489, 490.

*Primary Examiner*—Alan Siegel
*Attorney, Agent, or Firm*—Albert C. Johnston

[57] ABSTRACT

Preparation of a 3-thienylmalonic acid or a diester thereof comprising reacting in a polar solvent in the presence of a copper (I) halide a thiophene compound of formula:

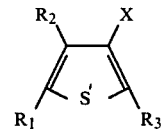

wherein
 X=I or Br,
 $R_1$=H or a $C_{1-4}$ alkyl group,
 $R_2$=H or a $C_{1-2}$ alkyl group and
 $R_3$=H or a $C_{1-2}$ alkyl group, with the proviso that $R_2$ and $R_3$ cannot be an alkyl group simultaneously, with a mono-deprotonated methylene compound of formula:

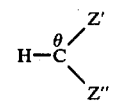

wherein a cation is present and Z'=Z" is CN or COOR in which R is a $C_{1-4}$ alkyl group, or Z'=CN and Z"=COOR' in which R' is a $C_{1-2}$ alkyl group, followed by hydrolysis by methods known per se to get the corresponding free acid.

12 Claims, No Drawings

PREPARATION OF A 3-THIENYLMALONIC ACID AND THE CORRESPONDING DIESTERS

This is a continuation-in-part of application Ser. No. 963,980 filed Nov. 24, 1978, now abandoned.

This invention relates to a method for the preparation of a 3-thienylmalonic acid, i.e. 3-thienylmalonic acid or 3-(alkyl substituted thienyl) malonic acids, as well as to the corresponding diesters. The invention further relates to a 3-thienylmalonic acid and the corresponding diesters thereof per se.

Diesters of 3-thienylmalonic acid and 3-thienylmalonic acid itself are useful intermediates in the preparation of specific semi-synthetic antibiotics, especially those of formula:

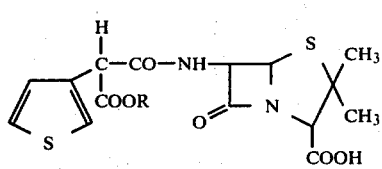

A few multistage processes for the preparation of 3-thienylmalonic acid or its diesters are known, all using a 3-thienylacetonitrile as an intermediate.

In the British patent specification No. 125,557 a route is described wherein 3-methylthiophene is converted to 3-thienylacetonitrile through bromination with N-bromosuccinimide and subsequent substitution with sodium cyanide. This route of classical design is completed by ethanolysis of the 3-thienylacetonitrile to ethyl 3-thienylacetate followed by carbo-alkoxylation in the α-position to give the desired diester of 3thienylmalonic acid.

Although this is the shortest route so far described in literature it has some serious disadvantages. The intermediate 3-bromomethylthiophene is an obnoxious compound which has to be prepared in a tedious way under strictly anhydrous conditions. Also the use of cyanide can be regarded as a drawback.

According to British patent specification No. 1,359,992 the required intermediate 3-thienylacetonitrile can be obtained by dehydrogenation of the Knoevenagel condensation product of tetrahydrothiophen-3-one and cyanoacetic acid. The starting compound tetrahydrothiophen-3-one is a relatively unstable intermediate which has to be prepared separately in two steps from methyl acrylate and methyl thioglycolate. The dehydrogenation step demands rather specific conditions i.e. using a partially poisoned tungsten oxide as a catalyst at a temperature of 430°–530° C. The overall yield of this lengthy reaction sequence is rather low.

A third way to prepare 3-thienylacetonitrile is mentioned in the British patent specification No. 1,359,991. Thiophene is chlorinated to 2,5-dichlorothiophene which is converted to 2,5-dichloro-3-cyanomethylthiophene through chloromethylation and subsequent substitution with sodium cyanide. Removal of the protective chlorine substituents in the 2- and 5-positions and ethanolysis of the cyanide function gives ethyl 3-thienylacetate. Conversion to a diester of 3-thienylmalonic acid is achieved as described above.

The drawbacks of this route are of the same order as those mentioned for the first route i.e.: the obnoxious character of the chloromethylation agent and the 2,5-dichloro-3-chloromethylthiophene as well as the use of sodium cyanide. Moreover, a low overall yield is obtained by a lengthy reaction sequence.

In addition to the prior art routes described above we attempted Knoevenagel condensations of tetrahydrothiophen-3-one with several derivatives of malonic acid with the intention that subsequent aromatization would directly lead to the desired derivatives of 3-thienylmalonic acid. It was anticipated that the dehydrogenation of this type of Knoevenagel products would need milder conditions than applied in the second route given above. However, out of the extensive number of agents known for this type of reaction a dehydrogenating agent that would afford the desired end products in reasonable yields could not be found.

A second approach was based on the rearrangement of arylacetyl compounds to methyl arylacetates by means of thallium trinitrate in methanol. Therefore 3-acetylthiophene was prepared from thiophene through chlorination in the 2- and 5-positions followed by acylation with aluminium trichloride and acetyl chloride and finally dechlorination. Rearrangement with thallium trinitrate in methanol gave methyl 3-thienylacetate in good yields, which can be used as a starting compound for the synthesis of 3-thienylmalonic acid or its diesters. Alternatively the rearrangement can be performed before the dechlorination step to give methyl 2,5-dichloro-3-thienylacetate which again can serve as a starting compound for the preparation of 3-thienylmalonic acid and its derivatives. The latter reaction order gives a lower, but still reasonable, yield compared to the former. However, the use of the expensive and highly toxic thallium reagent in these syntheses prevents an economically viable exploitation of this route.

Summarizing it can be said that all the routes described above show serious disadvantages of economic, toxicological and/or environmental nature.

The principal object of the invention is to provide a method for preparing a 3-thienylmalonic acid or its diester not showing the drawbacks of the aforementioned reactions.

Another object of the invention is to provide a preparation method by which new 3-thienylmalonic acids or their corresponding esters can be synthesized, thus creating the possibility of synthesizing new penicillins and cephalosporins.

The objects of the invention are met by a method for preparing a 3-thienylmalonic acid or a diester thereof characterized by reacting in a polar solvent in the presence of a copper (I) halide a thiophene compound of formula:

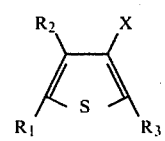

wherein
X=Br or I,
$R_1$=H or a $C_{1-4}$ alkyl group,
$R_2$=H or a $C_{1-2}$ alkyl group and
$R_3$=H or a $C_{1-2}$ alkyl group,
with the proviso that $R_2$ and $R_3$ cannot be an alkyl group simultaneously, with a monodeprotonated methylene compound of formula:

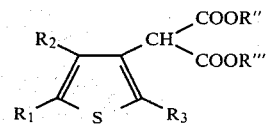

wherein:
(a) if $R_1=R_2=R_3=H$, either $R''$ and $R'''$ represent a methyl group; or $R''$ represents a $C_{1-4}$ alkyl group and $R'''$ a $C_{3-4}$ alkyl group;

or wherein:
(b) $R_1=H$ or a $C_{1-4}$ alkyl group,
$R_2=H$ or a $C_{1-2}$ alkyl group and
$R_3=H$ or a $C_{1-2}$ alkyl group,
with the proviso that $R_2$ and $R_3$ cannot be an alkyl group simultaneously and $R_1$, $R_2$ and $R_3$ are not H simultaneously, and $R''$ and $R'''$, which may be the same or different, represent a $C_{1-4}$ alkyl group.

The invention also provides and relates as well to 3-thienylmalonic acids prepared from the diester of (b) by hydrolytic methods known per se.

The following examples will serve to illustrate the invention. We would emphasize that the examples represent best the present state of affairs, but that actions to achieve optimum results have not yet been concluded, so that higher yields than those mentioned are most likely to be realizable.

EXAMPLE 1: PREPARATION OF DIETHYL 3-THIENYLMALONATE (a) with 3-iodothiophene and CuBr 15.6 g of a 80 percent suspension of NaH in mineral oil (=0.52 mole) were added portionwise at a temperature of 60° C. to a stirred solution of 90 g (=0.56 mole) diethyl malonate in 450 ml quinoline kept under dry $N_2$ atmosphere to effect mono-deprotonation of the malonate. After the liberation of hydrogen gas had been ceased 66.15 g (=0.32 mole) 3-iodothiophene and 50.5 g (=0.35 mole) copper (I) bromide were added. The mixture was stirred during a period of 4 hours at a temperature of 95° C. under $N_2$ atmosphere and then poured into a mixture of 500 g ice, 500 ml water and 500 ml concentrated HC1. The precipitated copper salts were collected on a Büchner funnel by filtration and washed with dichloroethane. The filtrate was extracted likewise with dichloroethane. Both dichloroethane phases were combined and then washed and dried. After removal of the solvent under reduced pressure the residue was fractionated in vacuo. The main fraction (56.6 g with a boiling range of 110°-122° C. at 1.5 mm Hg) contained 53.2 g (=0.22 mole) diethyl 3-thienylmalonate i.e. a yield of 69% calculated to the 3-iodothiophene started from.

(b) with 3-bromothiophene and CuBr

After completion in the way as described under (a) the reaction between 83 g (=0.52 mole) diethyl malonate dissolved in 500 ml quinoline and 15 g NaH (80% suspension in mineral oil), 81.5 g (=0.50 mole) 3-bromothiophene and 71.8 g (=0.50 mole) copper (I) bromide were added. The mixture was kept under $N_2$ atmosphere and stirred during a period of 4 hours at a temperature of 150° C. The stirring was continued at 170° C. another 2 hours. After the reaction product had been poured out into a mixture of ice and diluted hydrowherein a cation is present and $Z'=Z''$ is CN or COOR in which R is a $C_{1-4}$ alkyl group, or $Z'=CN$ and $Z''=COOR'$ in which $R'$ is a $C_{1-2}$ alkyl group; followed by hydrolysis by methods known per se to get the corresponding free acid.

Preferably the starting compound is a 3-iodothiophene—especially 3-iodothiophene itself—because it gives better yields under milder conditions than the corresponding 3-bromothiophene compound. If, however, $Z'=Z''=CN$ a 3-bromothiophene is a preferential compound too.

Examples of suitable solvents are N,N-dimethylformamide (DMF), hexamethylphosphoric acid triamide (HMPA) and quinoline. Quinoline is preferred because of the high yields obtained in the substitution reactions. Also the recycling of quinoline is simpler than the recovery of DMF and HMPA.

In addition to the said three solvents lower aliphatic alcohols and malonic esters can be used while a combination of the various solvents is useful too. If both $Z'$ and $Z''$ are COOR then the solvent preferably is a combination of a malonic ester $CH_2(COOR)_2$ and DMF whereas, if both $Z'$ and $Z''$ are CN the solvent preferably is ethanol or i-propanol. In general, however, the choice of the solvent is governed by the particular nucleophile used.

The copper (I) halide may be Cu(I)Cl, Cu(I)Br or Cu(I)I, as will be shown in the Examples, of which Cu(I)Br is preferred. The amount of Cu(I) halide to be used may lie between 0.1 and 2.0 equivalents per mole of said 3-halothiophene. Preferably between 0.4 and 1.2 equivalents of Cu(I) halide are used. The use of less than 0.4 equivalent of Cu(I) halide can be considered although incomplete conversion to the desired 3-thienylmalonate may be the result. This may, however, be compensated by the easy way in which the 3-halothiophene can be recovered. The copper salts resulting from the substitution reaction can be isolated by simple filtration after aqueous work-up, thus preventing laborious procedures for the recovery of the copper salts from effluents.

Reaction time and reaction temperature may vary quite widely. Good yields of 3-thienylmalonates are obtained at temperatures of 40°-170° C. in 0.1-10 hours. Best results are achieved in reaction times of between ½ and 4 hours at 60°-130° C.

The preparation method according to the invention furnishes versatile compounds having a wide field of applications in organic chemistry, expecially in the relatively new field of thiophene chemistry.

With the exception of only two compounds, i.e. methylethyl and diethyl 3-thienylmalonate, all esters and all alkyl-substituted 3-thienylmalonic acids prepared by the method of the invention are considered new. Consequently, the invention also relates to diesters of 3-thienylmalonic acids of formula:

chloric acid and had been worked up with dichloroethane in the way described under (a) 164 g of a crude reaction product was obtained. GLC analysis showed it to contain 13.5 g (=0.056 mole) diethyl 3-thienylmalonate. This means a yield of only 11%.

(c) with 3-iodothiophene and CuCl (1) with HMPA as solvent:

In the way described under (a) and (b) an equivalent amount of NaH was added under $N_2$ atmosphere to a solution of 2.4 g (=0.015 mole) diethyl malonate in hexamethylphosphoric acid triamide (HMPA). The liberation of hydrogen gas having ceased 3.15 g (=0.015 mole) 3-iodothiophene and 1.5 g (=0.015 mole) copper (I) chloride were added. While the temperature was maintained at 100° C. the mixture was stirred during a period of 3 hours, then poured out in a mixture of 100 ml water with 10 ml concentrated hydrochloric acid and subsequently worked up in the usual way with dichloroethane. GLC analysis showed that the crude reaction product contained 1.13 g (=0.0465 mole) diethyl 3-thienylmalonate, corresponding to a yield of 31%, together with 35% of the 3-iodothiophene started from. So, actually, the yield was 47% because the 3-iodothiophene can be recycled.

(2) with DMF as solvent:

The same experiment as mentioned under (1) but now using dimethylformamide (DMF) as solvent instead of HMPA and stirring at a temperature of 50° C. instead of 100° C. yielded a crude reaction product that according to GLC analysis contained 0.87 g (=0.0036 mole) diethyl 3-thienylmalonate, corresponding to a yield of 24%, and 10% of the 3-iodothiophene started from.

(d) with 3-bromothiophene and CuI

A mixture of 19.6 g (=0.12 mole) 3-bromothiophene and 34.2 g (=0.18 mole) copper (I) iodide in 100 ml quinoline was stirred while kept under a $N_2$ atmosphere during a period of 14 hours and at a temperature of 150° C. The mixture was allowed to cool down somewhat (approx. to 70°-80° C.). To determine the conversion degree of the reaction a 10 ml sample was drawn from the mixture, poured in diluted hydrochloric acid and the organic layer extracted with chloroform. GLC analysis showed conversion degree of 49%. To the rest of the reaction mixture was added a mixture of diethyl sodiummalonate in 190 ml quinoline, which latter mixture had been prepared from 3.84 g (=0.160 mole) NaH and an equimolar amount of diethyl malonate. The resulting mixture was stirred under $N_2$ atmosphere during a period of 3 hours and at a temperature of 100° C., then poured in iced diluted hydrochloric acid and subsequently worked up in the usual way (see under (a)). GLC analysis of the crude reaction product showed it to contain:

6.6 g (=0.027 mole) diethyl 3-thienylmalonate, corresponding to a yield of 25% (calculated to the 3-bromothiophene started from)

7.6 g (=43%) 3-bromothiophene 600 mg 3-iodothiophene (=2.7% calculated to the 3-bromothiophene).

Actually, the above reaction is considered to be a 2-stage reaction: first 3-bromothiophene is converted to 3-iodothiophene which, without isolating, is reacted further with diethyl sodiummalonate.

EXAMPLE 2: PREPARATION OF DI-T-BUTYL 3-THIENYLMALONATE

While keeping a solution of 8.65 g (=0.040 mole) di-t-butyl malonate in 45 ml quinoline under an atmosphere of dry $N_2$-gas and at a temperature of 60° C. 1.2 g of a 80 per cent suspension of NaH in mineral oil (corresponding to 0.040 mole NaH) were added portionwise. The liberation of hydrogen gas having ceased 6.72 g (=0.032 mole) 3-iodothiophene and 4.5 g (=0.032 mole) copper (I) bromide were added. While maintaining a $N_2$ atmosphere the mixture was stirred during a period of 3 hours at a temperature of 100° C.

Then the reaction mixture was poured out into an aqueous buffer solution (pH about 7) and worked up in the usual way.

GLC analysis showed that the rough reaction product contained 5.25 g (=0.0176 mole) di-t-butyl 3-thienylmalonate, corresponding to a yield of 55%.

This was isolated and purified in the following way. Using toluene as elution agent the crude reaction product was chromatographed over a column filled with silica gel. After those fractions containing the desired compound had been joined the solvent was removed under reduced pressure. The residue was chromatographed once again over a column filled with silica gel using petroleum ether 40-60 as elution agent. Those fractions containing the desired compound were joined, the solvent was evaporated and the residue (2.3 g) recrystallized at −18° C. from n-heptane. This resulted in 1.0 g of a crystalline compound melting at 41.2°-42.9° C.

EXAMPLE 3: PREPARATION OF DIETHYL 2,5-DIMETHYL-3-THIENYLMALONATE 0.6 of a 80 percent suspension of NaH in paraffin (=0.020 mole) were added portionwise at a temperature of 60° C. to a stirred solution of 3.22 g (=0.020 mole) diethyl malonate in 45 ml quinoline kept under dry $N_2$ atmosphere.

After the liberation of hydrogen gas had been ceased 3.57 g (=0.015 mole) 2,5-diemthyl-3-iodo-thiophene and 2.15 g (=0.015 mole) copper (I) bromide were added to this solutin of mono-deprotonated diethyl malonate.

The mixture was stirred during a period of 3 hours at a temperature of 100° C. under $N_2$ atmosphere and then poured into 150 ml 4N HCl.

After removal of the precipitated copper salts by filtration the mixture was extracted with chloroform and the chloroform extract dried over magnesium sulphate. GLC analysis of the dried solution showed it to contain—apart from 1.8 g (=51%) non-reacted 2,5-dimethyl-3-iodothiophene—1.1 g diethyl 2,5-dimethyl13-thienylmalonate, corresponding to a yield of 27%. This mixture after removal of the chloroform was chromatographed over a column filled with silica gel using 9:1 mixture of toluene and ethyl acetate as elution agent.

The desired product was identified by NMR and IR.

EXAMPLE 4: PREPARATION OF DIETHYL 2,5-DIETHYL-3-THIENYLMALONATE 1.2 g of a 80 percent suspension of NaH in paraffin (=0.040 mole) were added portionwise at a temperature of 60° C. to a stirred solution of 6.4 (=0.040 mole) diethyl malonate in 45 ml quinoline kept under dry $N_2$ atmosphere.

After the liberation of hydrogen gas had been ceased 8.51 g (=0.032 mole) 2,5-diethyl-3-iodothiophene and 4.6 g (=0.032 mole) copper (I) bromide were added to this solution of mono-deprotonated diethyl malonate. The mixture was stirred during a period of 3 hours at a temperature of 100° C. under $N_2$ atmosphere and then poured into a mixture of 45 g ice and 45 ml concentrated HCl.

After removal of the precipitated copper salts by filtration the mixture was extracted with chloroform, the chloroform extract washed with an aqueous solution of sodium bicarbonate and dried over magnesium sulphate. From a sample of this residue the chloroform was evaporated and the resulting mixture chromatographed over a column filled with silica gel using a 9:1 mixture of toluene and ethyl acetate as elution agent. The desired ester was obtained in pure form and identified by NMR. With the aid of this pure sample the reaction yield was determined by means of GLC analysis: apart from 22% of unreacted 2,5-diethyl-3-iodothiophene, 21% diethyl 2,5-diethyl-3-thienylmalonate was found. If the yield of the latter were calculated to the amount of consumed 2,5-diethyl-3-iodothiophene the yield would rise to 27%.

EXAMPLE 5: PREPARATION OF DI-TERT-BUTYL 2,5-DIMETHYL-3-THIENYLMALONATE

After deprotonation in the usual way of 8.65 g (=0.040 mole) di-tert-butyl malonate in quinoline the resulting mixture was stirred during a period of 3 hours at a temperature of 100° C. in the presence of 4.6 g (=0.032 mole) copper (I) bromide and 7.62 g (=0.032 mole) 2,5 -dimethyl-3-iodothiophene.

The reaction mixture was then poured into an aqueous buffer solution of pH 7 and worked up in the way mentioned above.

After extraction with chloroform and removal of the solvent an oil was obtained which according to GLC analysis contained 3.2 g (=42%) non-reacted 2,5-dimethyl-3-iodothiophene and 2.1 g (=25%) non-reacted di-tert-butyl malonate. Though from GLC analysis the presence of di-tert-butyl 2,5-dimethyl-3-thienylmalonate was not certain the reaction mixture was chromatographed over a column filled with silica gel using toluene as elution agent. The fractions that are to contain the desired product were joined and the solvent evaporated under reduced pressure. The residue was crystallized from petroleum-ether which resulted in 0.71 g (=6.8%) of a crystalline product. This was recrystallized from petroleum-ether after which a 0.15 g sample melting at 78.2°–79.8° C. was obtained. The identification of the desired product was completed by NMR analysis and IR spectroscopy.

EXAMPLE 6: PREPARATION OF DIETHYL 4-METHYL-3-THIENYLMALONATE 1.2 of a 80 percent suspension of NaH in mineral oil (=0.040 mole) were added portionwise at a temperature of 60° C. to a stirred solution of 6.4 g (=0.040 mole) diethyl malonate in 45 ml quinoline kept under dry $N_2$ atmosphere.

After the liberation of hydrogen gas had been ceased 7.2 g (=0.032 mole) 3-iodo-4-methylthiophene and 4.6 g (=0.032 mole) copper (I) bromide were added. The mixture was stirred during a period of 3 hours at a temperature of 100° C. and then poured into a mixture of 100 ml water and 45 ml concentrated HCl. The precipitated copper salts were collected on a Büchner funnel by filtration and washed with chloroform. After the filtrate was extracted likewise with chloroform the chloroform layers were joined and dried over magnesium sulphate. After removal of the solvent GLC analysis of the residue (12.9 g) showed it to contain 4.06 g diethyl 4-methyl-3-thienylmalonate (=0.016 mole or 50% calculated to the 3-iodo-4-methylthiophene started from). A pure sample was obtained by chromatography over a column filled with silica gel using toluene-ethyl acetate 20:1 as elution agent. Identification of the produce was carried out by NMR and IR spectroscopy.

EXAMPLE 7: PREPARATION OF DIMETHYL 3-THIENYLMALONATE

In the way described before 5.3 g (=0.040 mole) dimethyl malonate were mono-deprotonated with 0.040 mole NaH in 75 ml quinoline. Then 6.7 g (=0.032 mole) 3-iodothiophene and 4.6 g (=0.032 mole) copper (I) bromide were added. The resulting mixture was stirred under $N_2$ atmosphere during a period of 4.5 hours at a temperature of 80° C. and then poured out into a mixture of 75 ml water and 75 ml concentrated HCl. The precipitated copper salts were collected on a Büchner funnel and washed with chloroform. Extraction of the filtrate occured likewise with chloroform. Both chloroform layers were joined and dried over magnesium sulphate. After removal of the solvent 11.0 g of an oily product remained in which by GLC analysis the presence was demonstrated of 1.93 g 3-iodothiophene and 1.32 g di-methyl 3-thienylmalonate (=0.006 mole or 19% calculated to the 3-iodothiophene started from). The product was identified in the same way as described in Example 5.

EXAMPLE 8: PREPARATION OF DI-ISOPROPYL 3-THIENYLMALONATE

In the way described before 18.8 g (=0.10 mole) di-isopropyl malonate were mono-deprotonated with 0.10 mole NaH in 112.5 ml quinoline. After the liberation of hydrogen gas had been ceased 16.8 g (=0.080 mole) 3-iodothiophene and 11.5 g (=0.080 mole) copper (I) bromide were added. The resultant mixture was stirred under $N_2$ atmosphere at a temperature of 100° C. during a period of 5 hours and subsequently poured out into an icy-cold mixture of 112 ml water and 112 ml concentrated HCl. The precipitated copper salts were collected on a Büchner funnel and washed with chloroform. The filtrate was extracted with chloroform too. The two chloroform layers were joined and dried over magnesium sulphate. After removal of the solvent a residue remained which according to GLC analysis contained 0.44 g 3-iodothiophene and 12 g di-isopropyl 3-thienylmalonate (=0.044 mole or 55% calculated to the 3-iodothiophene started from). A pure sample was obtained by chromatography over a column filled with silica gel using toluene as elution agent. The product so obtained could be crystallized at −18° C. from petroleum ether 40-60; at room temperature, however, it is a liquid. Identification of the purified product occurred through NMR and IR spectroscopy.

EXAMPLE 9

Example 9 (A+B) is directed to the preparation of diethyl-3-thienylmalonate by reaction of 3-halothiophene with the ethyl ester of α-cyano-acetic acid followed by hydrolysis and esterification.

A. Reaction with α-cyano-ethylacetate (a) To 150 ml DMF, kept under $N_2$ atmosphere, were added while stirring 0.12 mole α-cyano-ethylacetate, 0.12 mole anhydrous $K_2CO_3$, 0.12 mole CuBr and 0.1 mole 3-iodothiophene.

The reaction mixture was stirred at 40° C. for 2 hours, at 60° C. for 1 hour and at 80° C. for 2.5 hours. Thereafter the reaction mixture was cooled to room temperature and poured out into diluted HCl. The precipitated copper salts were collected on a Büchner funnel and washed with chloroform. Extraction of the filtrate occurred likewise with chloroform. Both chloroform layers were joined and dried over magnesium sulphate. After removal of the solvent the remaining oily product was fractionated under reduced pressure. The first runnings (28.2 g with a boiling point of 100° C. at 20-40 mm Hg) contained 11.3 g or 54% unreacted 3-iodothiophene. At 105°-115° C./0.4 mm Hg were obtained 5.7 g (=26% calculated to the amount of 3-iodothiophene started from) ethyl 3-thienyl-α-cyanoacetate, which was identified through NMR and IR spectroscopy.

In an analogous way 0.1 mole 3-iodothiophene and 0.15 mole α-cyano-ethylacetate were reacted to ethyl 3-thienyl-α-cyanoacetate under the following conditions:

(b) with 0.15 mole $(CH_3)_3$COK and 0.1 mole CuBr in 80 ml of a mixture of ethanol (abs.) and DMF during 2 hours at 60° C.

Yield: 28% and 41% unreacted 3-iodothiophene.

(c) with 0.15 mole $(CH_3)_3$COK and 0.1 mole CuBr in 80 ml DMF during 3 hours at 70° C.

Yield: 24% and 42% unreacted 3-iodothiophene.

(d) with 0.15 mole $LiOC_2H_5$ and 0.1 mole CuBr in 80 ml of a mixture of ethanol (abs.) and DMF during 2 hours at 60° C.

Yield: 23% and 38% unreacted 3-iodothiophene.

(e) with 0.15 mole $NaOC_2H_5$ and 0.1 mole CuBr in 80 ml of a mixture of ethanol (abs.) and DMF during 2 hours at 80° C.

Yield: 20% and 52% unreacted 3-iodothiophene.

(f) and starting from 3-bromothiophene with 0.15 mole $(CH_3)_3$COK and 0.1 mole CuBr in 80 ml quinoline during 1 hour at 70° C. the yield was 17% with 50% of unreacted 3-bromothiophene.

B. Hydrolysis and esterification step

About 10 g HCl gas was led into 35 ml freshly over Mg distilled ethanol and to this mixture 0.03 mole of water and 0.03 mole of ethyl 3-thienyl-α-cyanoacetate were added. The resulting mixture was stirred for ½ hour at room temperature and then for 1 hour at reflux temperature. The reaction mixture was poured out into 600 ml water and the organic layer separated from the aqueous layer. The latter was extracted with chloroform (three times with 40 ml portions) and the chloroform extractions were combined with the organic layer to one organic phase. The organic phase was dried over magnesium sulphate and the solvent removed by evaporation.

The residue was fractionated by bulb to bulb distillation (approx. 0.3 mm Hg/110° C.). The yield of diethyl 3-thienylmalonate was 5.5 g or 76%. The product was identified by means of IR and NMR spectroscopy.

Examples 10 and 11 are directed to the preparation of diethyl 3-thienylmalonate by reaction of a 3-halothiophene with malonitrile followed by hydrolysis and esterification. Example 10 illustrates a reaction in two separate steps i.e. with isolation of the intermediate 3-thienylmalonitrile whereas in Example 11 the reaction is carried out in one continued operation.

EXAMPLE 10

A. Reaction with malonitrile (a) To 150 ml anhydrous ethanol, kept under $N_2$ atmosphere, were added while stirring at 40° C. 0.2 mole NaH and 0.2 mole malonitrile. After 10 minutes of stirring at 40° C. 0.1 mole CuBr and 0.1 mole 3-bromothiophene were added. The pale yellow suspension was refluxed for 2 hours and then poured into 700 ml water and 50 ml concentrated HCl. After filtration (Büchner funnel) the filtrate was extracted with chloroform. After the usual steps of drying and evaporating the solvent, the residue was purified by means of column chromatography over silica gel (0.05-0.2 mm) using toluene as eluent. After removal of toluene yellow 3-thienylmalonitrile (m.p. 40.8°-41.4° C.) resulted in a yield of 39%, based on the amount of 3-bromothiophene started from.

As also 29% of unreacted 3-bromothiophene was recovered the actual yield was 55%.

(b) In an analogous way but using i-propanol (p.a.) instead of ethanol and refluxing 3.75 hours instead of 2, 75% of unreacted 3-bromo-thiophene and 19% 3-thienylmalonitrile were obtained. Based on reacted 3-bromothiophene the (actual) yield was 76%.

B. Hydrolysis and esterification step

Approx. 7 g HCl gas was led into 33 ml anhydrous ethanol and thereafter 0.06 mole water and 0.03 mole 3-thienylmalonitrile were added. The reaction mixture was refluxed for 1.5 hours and then poured out into 600 ml of water. After the usual steps of extracting (with chloroform), drying (over $MgSO_4$) and evaporating of the solvent crude diethyl 3-thienylmalonate in a yield of 90% was obtained. After purification by means of bulb to bulb distillation the pure product was identified by IR and NMR spectroscopy.

EXAMPLE 11

In the way as described in Example 10 A. a suspension of 150 ml anhydrous ethanol, 0.2 mole NaH, 0.2 mole malonitrile, 0.1 mole CuBr and 0.1 mole 3-bromo-thiophene were brought to reflux. After 3 hours of refluxing another 0.025 mole CuBr was added and the refluxing contiued for 1 hour. Thereafter an excess of HCl gas was led into the reaction mixture and 0.4 mole water added. The HCl flow and reflux were continued for another 2 hours. After the usual working up and purification steps the following products were obtained:
(a) unreacted 3-bromothiophene, yield 38%
(b) diethyl 3-thienylmalonate, yield 32%
(c) ethyl 3-thienylacetate, yield 3%.

If the yield of diethyl 3-thienylmalonate were calculated to the amount of consumed 3-bromothiophene the yield rises to approx. 52%.

EXAMPLE 12: PREPARATION OF 3-THIENYLMALONITRILE

To 157.5 ml anhydrous i-propanol and 17.5 ml DMF, kept under $N_2$ atmosphere, were added while stirring at 20°-35° C. 0.2 mole NaH and then, after the sodium isopropylate had been precipitated, 0.2 mole malonitrile. Within 5 minutes thereafter 0.1 mole copper (I) bromide and 0.1 mole 3-bromothiophene were added.

The suspension was refluxed at approx. 80° C. for 3 hours and poured out in a mixture of 1000 ml water and 100 ml concentrated HCl. The copper salts were filtered off and washed with chloroform (3×100 ml). The aqueous layer was extracted with chloroform (2×100 ml) and all chloroform layers combined to one organic phase. The organic phase was dried over magnesium sulphate and the chloroform evaporated until a volume of approx. 130 ml remained. GLC analysis showed it to contain about 27% of 3-thienylmalonitrile apart from about 12% of unreacted 3-bromothiophene.

EXAMPLE 13

This Example illustrates the conversion of the diester to the acid: A stirred mixture of 160 ml water, 0.89 mole NaOH and 165 ml ethanol was brought to reflux and then quickly 0.36 mole diethyl 3-thienylmalonate was added. Stirring and refluxing were continued for ½ hour and then the reaction mixture was distilled until the distillation temperature rised above 95° C. After cooling the residue to about 20° C. approx. 170 ml of a rather viscous liquid remained. This residue was added while stirring to 105 ml (=abt.1 mole) HCl of 18°-20° C. in about 45 minutes. Cooling was needed to keep the temperature at 18°-20° C. Thereafter the reaction mixture was further cooled to 0° C. and stirred for ½ hour at 0°-2° C. The crude 3-thienylmalonic acid was collectioned on a Büchner funnel and washed twice with ice water. After drying the yield was 88%.

EXAMPLE 14: PREPARATION OF DIMETHYL 3-THIENYLMALONATE

Whereas in Example 7 dimethyl 3-thienylmalonate was prepared with quinoline as solvent in this Example its preparation will be illustrated using a lower aliphatic alcohol (methanol), in combination with DMF, as solvent:

10.8 g NaOCH$_3$ in 40 ml methanol were added to 28 g stirred dimethylmalonate. After addition of 16 ml DMF and 16 g copper (I) bromide 21 g 3-iodothiophene were dosed within 15 minutes at 95° C.

After about 45 minutes the reaction mixture was worked up in a way analogous as to that mentioned in Example 15, except for the distillation step. The yield was about 15.8 g of a crude product, containing according to GLC analysis the desired compound as the main component.

EXAMPLE 15: PREPARATION OF DI-ISOPROPYL-3-THIENYLMALONATE

Whereas in Example 8 di-isopropyl-3-thienylmalonate was prepared within quinoline as solvent, in this Example its preparation will be illustrated using isopropyl alcohol in combination with DMF as solvent: 13.5 g of a 57 percent suspension of NaH in mineral oil and 75 g diisopropylmalonate were added portionwise to 100 ml stirred isopropyl alcohol. The temperature was raised to 90° C. and, while isopropyl alcohol was distilled off, 22 ml DMF and 22 g copper (I) chloride were added. To this mixture, at 90°-95° C., 42 g 3-iodothiophene were added portionwise and the whole maintained at this temperature for about 2 hours. Then 200 ml toluene were added and, after the mixture had been cooled down to room temperature, 20 ml acetic acid were added. The copper salts were filtered on a Büchner funnel, washed twice with 100 ml portions of toluene and this toluene solution combined with the organic layer that was separated from the filtrate. After evaporation of the solvents the residue was distilled at approx. 1 mm Hg. The yield was 31.1 g or 60%.

EXAMPLE 16: PREPARATION OF DIETHYL 3-THIENYLMALONATE

Whereas in Example 1 diethyl 3-thienylmalonate was prepared with quinoline as solvent in this Example its preparation will be illustrated using a combination of a malonic ester and DMF as solvent.

30 g NaOCH$_3$ were added portionwise to 200 ml stirred diethylmalonate and under reduced pressure alcohol was distilled off until a bottom temperature of 95° C. was reached. After addition of 40 ml DMF the remaining alcohol was distilled off and then 39.5 g copper (I) bromide were added followed by dosing 55.3 g 3-iodothiophene at 90°-100° C. within 15 minutes. Stirring at this temperature was continued for another 15 minutes and thereafter 250 ml toluene and 30 ml acetic acid were added. The precipitated copper salts were filtered off and washed with toluene. The organic reaction layer was separated from the aqueous layer, washed with 125 ml water acidified with 10 ml concentrated HCl and then two times with 100 ml water. The organic layer was combined with the toluene wash layer to one organic phase which was dried over magnesium sulphate. After evaporation of the solvent 200.5 g of a crude product was obtained which upon distillation yielded 50 g=82.7% of the pure ester.

EXAMPLE 17: PREPARATION OF MIXED 3-THIENYLMALONATES 43.2 g NaOCH$_3$ were added to 250 ml stirred isopropyl alcohol and alcohols (50 ml) was distilled off until the bottom temperature was 100° C. After addition of 144 g diethyl malonate another 130 ml alcohols were distilled off at reflux temperature (approx. 85° C.).

DMF (55 ml) and copper (I) chloride (55 g) were added, the temperature was raised to about 100° C. and then 94.5 g 3-iodothiophene were added. After 2 hours the reaction was stopped, although GLC analysis showed that the reaction had not yet been completed.

The reaction mixture was worked up as mentioned in Example 15. The yield after distillation was about 60%.

Although the reaction product in this case is a mixture of almost inseparable esters—for there are 6 esters possible—upon saponification it affords only one product: 3-thienylmalonic acid. Consequently, where the acid is the desired end product it does not matter that the reaction product comprises more than one ester.

EXAMPLE 18: PREPARATION OF THE MIXED DIESTER ETHYL T-BUTYL-3-THIENYL-MALONATE 0.040 mole NaH (used as an 80 percent suspension in paraffin) was added portionwise at a temperature of 60° C. to a stirred solution of 0.040 mole ethyl t-butyl malonate in 45 ml quinoline kept under dry N$_2$ atmosphere. After the liberation of hydrogen gas had ceased, 0.032 mole 3-iodothiophene and 0.032 mole copper (I) bromide were added.

The mixture was stirred for 3 hours at a temperature of 100° under an N$_2$ atmosphere and then poured into a mixture of 500 ml cold water, buffered at pH 7. The precipitated copper salts were collected by filtration on a Büchner funnel and washed with chloroform. The filtrate was extracted with 3×30 ml chloroform. The chloroform phases were combined and then washed and dried.

After isolation by means of column chromatography the desired ethyl t-butyl 3-thienylmalonate was obtained in 50% yield, calculated to the amount of the 3-iodothiophene started from. As the starting 3-iodothiophene was recovered in 19% yield, the actual yield of the diester was almost 60%. GLC analysis, however, showed this product to be contaminated with about 15% by weight of ethyl t-butyl malonate. Neither diethyl nor di-t-butyl 3-thienylmalonate was found to be present in the GLC. The reaction product was identified with the aid of NMR and IR spectroscopy.

Mixed diesters thus prepared create the possibility of a new route to monoesters of 3-thienylmalonic acid and derivatives thereof.

We claim:

1. A method for the preparation of a 3-thienylmalonic acid or a diester thereof comprising reacting in a polar solvent in the presence of copper (I) chloride, bromide or iodide, a thiophene compound of formula:

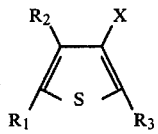

wherein $X = I$ or Br, $R_1 = H$ or a $C_{1-4}$ alkyl group, $R_2 = H$ or a $C_{1-2}$ alkyl group and $R_3 = H$ or a $C_{1-2}$ alkyl group, with the proviso that $R_2$ and $R_3$ cannot be an alkyl group simultaneously, with a mono-deprotonated methylene compound of formula:

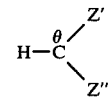

wherein a cation is present and $Z' = Z''$ is CN or COOR in which R is a $C_{1-4}$ alkyl group, or $Z' = CN$ and $Z'' = COOR'$ in which $R'$ is a $C_{1-2}$ alkyl group, followed when a said acid is desired by hydrolysis of the reaction product to get the corresponding free acid.

2. A method as claimed in claim 1 in which $X = I$.

3. A method as claimed in claim 1 in which $X = Br$ and $Z' = Z'' = CN$.

4. A method as claimed in claim 1, 2 or 3 in which the solvent is quinoline, N,N-dimethylformamide, hexamethyl phosphoric acid triamide, a lower aliphatic alcohol or a malonic ester, or a combination thereof.

5. A method as claimed in claim 1 or 2 in which the solvent, if both $Z'$ and $Z''$ are COOR, is a combination of a malonic ester $CH_2(COOR)_2$ and N,N-dimethylformamide.

6. A method as claimed in claim 1 or 2 in which the solvent, if both $Z'$ and $Z''$ are CN, is ethanol or i-propanol.

7. A method as claimed in claim 1 or 2 in which the reacting is effected in the presence of copper (I) bromide.

8. A method as claimed in claim 1 or 2 in which $X = I$ and $R_1 = R_2 = R_3 = H$.

9. A method as claimed in claim 4 in which $X = I$ and $R_1 = R_2 = R_3 = H$.

10. A method as claimed in claim 1 or 2 in which the copper (I) halide is present in an amount of 0.4 to 1.2 mole per mole of said thiophene compound.

11. A method as claimed in claim 1 or 2 in which the reaction is carried out at 60°–130° C. in ½–4 hours.

12. A method as claimed in claim 1 in which: $X = I$ and $R_1 = R_2 = R_3 = H$; the solvent is quinoline, N,N-dimethylformamide, hexamethyl phosphoric acid triamide, a lower aliphatic alcohol or a malonic ester, or a combination thereof; and the reacting is effected in the presence of copper (I) bromide in an amount of 0.4 to 1.2 mole per mole of said thiophene compound.

* * * * *